(12) United States Patent
Ko

(10) Patent No.: US 8,402,578 B2
(45) Date of Patent: Mar. 26, 2013

(54) HEATING AND STERILIZING APPARATUS FOR BED MATTRESS

(76) Inventor: Ho Jin Ko, Seongnam-si (KR)

( * ) Notice: Subject to any disclaimer, the term of this patent is extended or adjusted under 35 U.S.C. 154(b) by 533 days.

(21) Appl. No.: 12/537,737

(22) Filed: Aug. 7, 2009

(65) Prior Publication Data

US 2010/0319125 A1    Dec. 23, 2010

(30) Foreign Application Priority Data

Jun. 19, 2009    (KR) .................. 10-2009-0054963

(51) Int. Cl.
*A47C 21/04* (2006.01)
(52) U.S. Cl. .................. 5/423; 5/421; 5/706; 5/726
(58) Field of Classification Search ............. 5/421, 423, 5/706, 708, 710–713, 724, 726, 652.1, 652.2
See application file for complete search history.

(56) References Cited

U.S. PATENT DOCUMENTS

| | | | | |
|---|---|---|---|---|
| 4,777,802 A | * | 10/1988 | Feher | 62/3.3 |
| 5,652,987 A | * | 8/1997 | Fujita | 5/726 |
| 7,240,386 B1 | * | 7/2007 | McKay et al. | 5/724 |
| 7,950,084 B1 | * | 5/2011 | McKay et al. | 5/423 |
| 2007/0000061 A1 | * | 1/2007 | Chung | 5/706 |
| 2007/0033733 A1 | * | 2/2007 | Jen | 5/423 |
| 2009/0078690 A1 | * | 3/2009 | Lee et al. | 219/217 |
| 2011/0115635 A1 | * | 5/2011 | Petrovski et al. | 340/584 |
| 2011/0138539 A1 | * | 6/2011 | Mahoney et al. | 5/713 |

FOREIGN PATENT DOCUMENTS

KR    20-0373763    1/2005

* cited by examiner

*Primary Examiner* — William Kelleher
(74) *Attorney, Agent, or Firm* — Garcia-Zamor IP Law; Ruy M. Garcia-Zamor

(57) ABSTRACT

Provided is a heating and sterilizing apparatus. The heating and sterilizing apparatus for a bed mattress having a surface sheet constituting a top surface, a built-in elastic member for elastically supporting the surface sheet, and walls forming a front surface, a rear surface, and both side surfaces includes a mattress body providing a inner space, the mattress body having an installation hole, in which a portion of either side surface thereof is cut, a partition disposed inside the mattress body to partition the inner space defined inside the mattress body, a case disposed on the installation hole defined in the mattress body, and a heating and sterilizing part disposed in the case to heat and sterilize the inner space of the mattress body partitioned by the partition and calculate air within the inner space of the mattress body.

12 Claims, 7 Drawing Sheets

HEATING AND STERILIZING APPARATUS FOR BED MATTRESS

CROSS-REFERENCE TO RELATED APPLICATIONS

This application claims priority under 35 U.S.C. §119 to Korean Patent Application No. 10-2009-0054963, filed on Jun. 19, 2009, the disclosure of which is incorporated herein by reference in its entirety.

TECHNICAL FIELD

The present invention relates to a heating and sterilizing apparatus for a bed mattress, and more particularly, to a heating and sterilizing apparatus for a bed mattress in which a heating mode is freely set according to user's requirements during heating of the bed mattress, anions and cations are generated to prevent bacteria and molds from being propagated, and only a desired portion of the bed mattress is heated by selecting a split heating mode or a simultaneous heating mode, thereby always maintaining the bed mattress in a warm and clean state.

BACKGROUND

Generally, a bed mattress is covered with a smooth cloth cover, and an elastic member including a cushion is disposed therein. Also, the interior of the bed mattress is structurally sealed to cause bad ventilation.

Bad ventilation causes propagation of various bacteria, molds, and ticks in bed mattresses. As a result, various diseases such as allergic rhinitis, skin diseases, etc., may be caused.

Technologies for reducing mattress pollution and restraining propagation of various bacteria, molds, and ticks have been disclosed in Korean Utility Model No. 0373763, titled "bed mattress cleaning apparatus", applied by the same applicant as the present invention. The bed mattress cleaning apparatus provides a bed mattress that can reduce mattress pollution and restrain propagation of bacteria and germs to maintain a clean state.

According to the bed mattress cleaning apparatus, moisture within the mattress is removed using a dehumidification heater, and air within the mattress freely flows by an air-circulation fan. In addition, ultraviolet rays are irradiated to sterilize bacteria, and anions and ozone are supplied to remove stench. Thus, since dehumidification, sterilization, and deodorization processes are performed, the mattress can be maintained in a clean state. That is, the bed mattress cleaning apparatus is an apparatus for continuously maintaining bed mattress in clean condition.

Apart from the cleanness of the mattress, there is an apparatus for heating the mattress. A direct-heating type mattress is well-known as the apparatus for heating the mattress. According to the direct-heating type mattress, a built-in heater may be directly installed in a mattress to adjust a temperature of the mattress. Alternatively, a separate heating mat (e.g., an electric blanket) may be spread on the mattress to increase a surface temperature of the mattress during the most intense cold weather and the winter.

However, the mattress including the built-in heater has limitations that the heater should heat an entire surface of the mattress because the mattress has a structure in which the heater does not partially heat a desired portion with respect to a wide surface area. Thus, power consumption increases.

For example, when a user intends to heat only a portion (one side of a double bed mattress) of the mattress, it is impossible to selectively heat only the desired portion. Thus, the heater runs more than needs to increase power consumption. In case where a separate heating mat is spread on the mattress, a heater contacts a human body to expose the human body to electromagnetic waves and affect the human body even through the heater may partially and selectively heat a desired portion to reduce power consumption. In case of indoor heating, excessive heating energy may be used for heating an indoor.

As described above, although technologies for maintaining good ventilation and preventing various bacteria, molds, and ticks from being propagated to maintain a clean state, as well as technologies for heating a bed mattress are previously well-known in the art, technologies with respect to a bed mattress that is maintained in a clean state and selectively heated at a desired portion during the most intense cold weather and the winter are not yet known.

SUMMARY

Accordingly, the present invention provides a mattress, which is separately adjusted in surface temperature according to a user's selection and has a higher heat dissipation rate, superior heat generation capacity, safety, and low power consumption when compared to a conventional heating method.

The present invention also provides a mattress in which a heating energy is saved, and a heater generates tourmaline anions to stimulate metabolism of human body cells, boost vitality, and recover fatigue due to tourmaline anion effects during the bed mattress life, thereby allowing a user to keep a healthy bed life, and also, ozone is generated through an ozone lamp to prevent bacteria and molds within an inner space of a mattress body from being propagated, and simultaneously, to remove stench, thereby maintaining a clean state for a long time.

The present invention also provides a mattress that saves a heating energy according to a user's direct heating and reduces management expenses due to electricity usage.

According to an aspect, there is provided a heating and sterilizing apparatus for a bed mattress having a surface sheet constituting a top surface, a built-in elastic member for elastically supporting the surface sheet, and walls forming a front surface, a rear surface, and both side surfaces, the heating and sterilizing apparatus including: a mattress body providing a inner space, the mattress body having an installation hole, in which a portion of either side surface thereof is cut; a partition disposed inside the mattress body to partition the inner space defined inside the mattress body; a case disposed on the installation hole defined in the mattress body; and a heating and sterilizing part disposed in the case to heat and sterilize the inner space of the mattress body partitioned by the partition and calculate air within the inner space of the mattress body.

The partition may be longitudinally disposed along a length direction to symmetrically divide the inner space of the mattress body into both sides.

The heating and sterilizing part may include: a heater disposed inside the case to adjust a temperature of the inner space of the mattress body; an air-circulation fan disposed inside the case to circulate air within the inner space of the mattress body; an ozone lamp disposed at a central portion of the case to generate ozone; a temperature sensor detecting a temperature of the inner space of the mattress body; and an operation circuit part controlling operations of the heater, the air-circulation fan, and the ozone lamp.

The heating and sterilizing part may include a temperature overheat sensor in the inner space of the mattress body to detect an overheat temperature of the inner space of the mattress body and check the overheat temperature of the heater, thereby to transmit a detection signal to the operation circuit part and the external operation controller.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF EMBODIMENTS

Hereinafter, specific embodiments will be described in detail with reference to the accompanying drawings. The present invention may, however, be embodied in different forms and should not be construed as limited to the embodiments set forth herein. Rather, these embodiments are provided so that this invention will be thorough and complete, and will fully convey the scope of the present invention to those skilled in the art.

Figure 1:
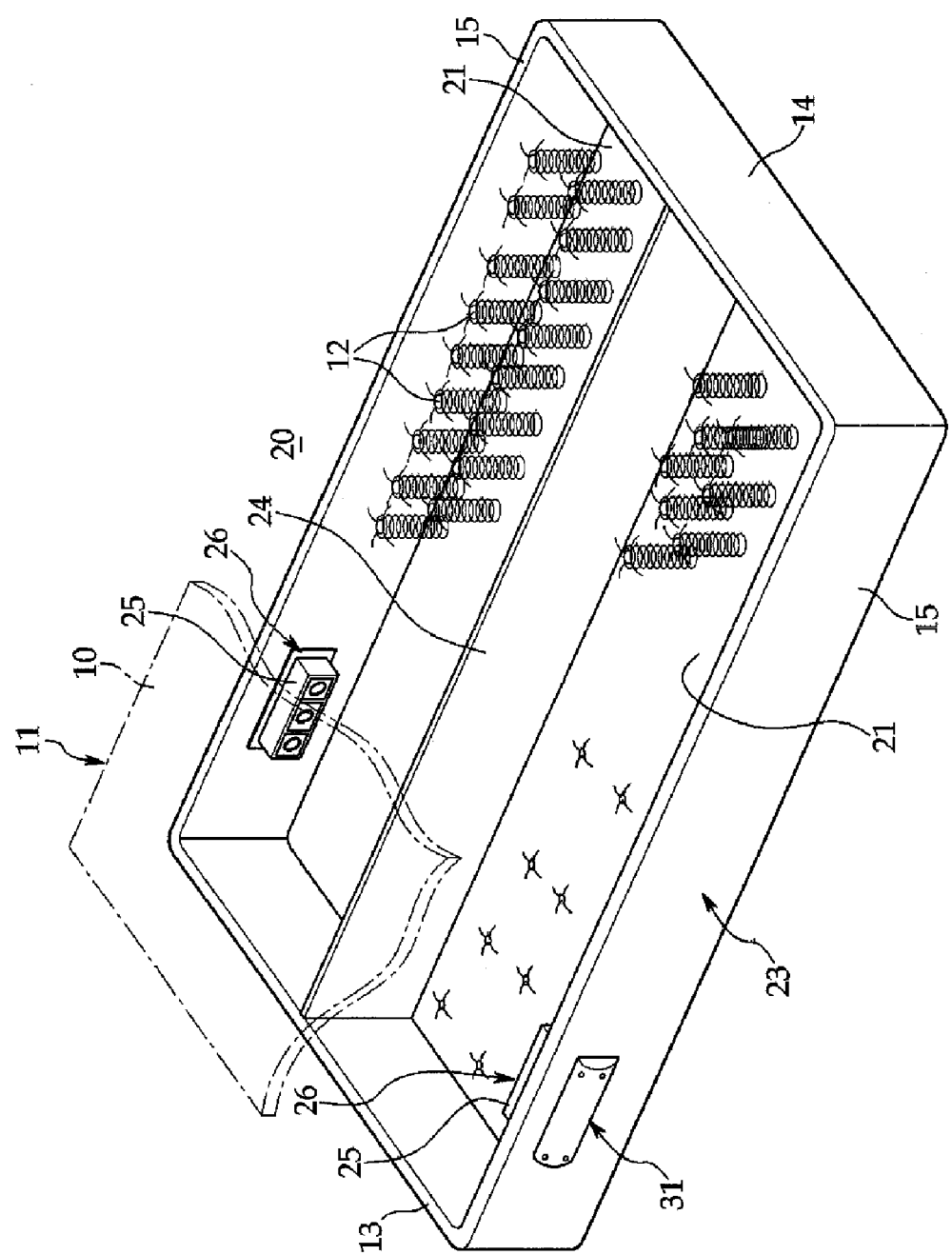
FIG. 1 is a perspective view of a bed mattress according to an embodiment of the present invention.
Figure 2:
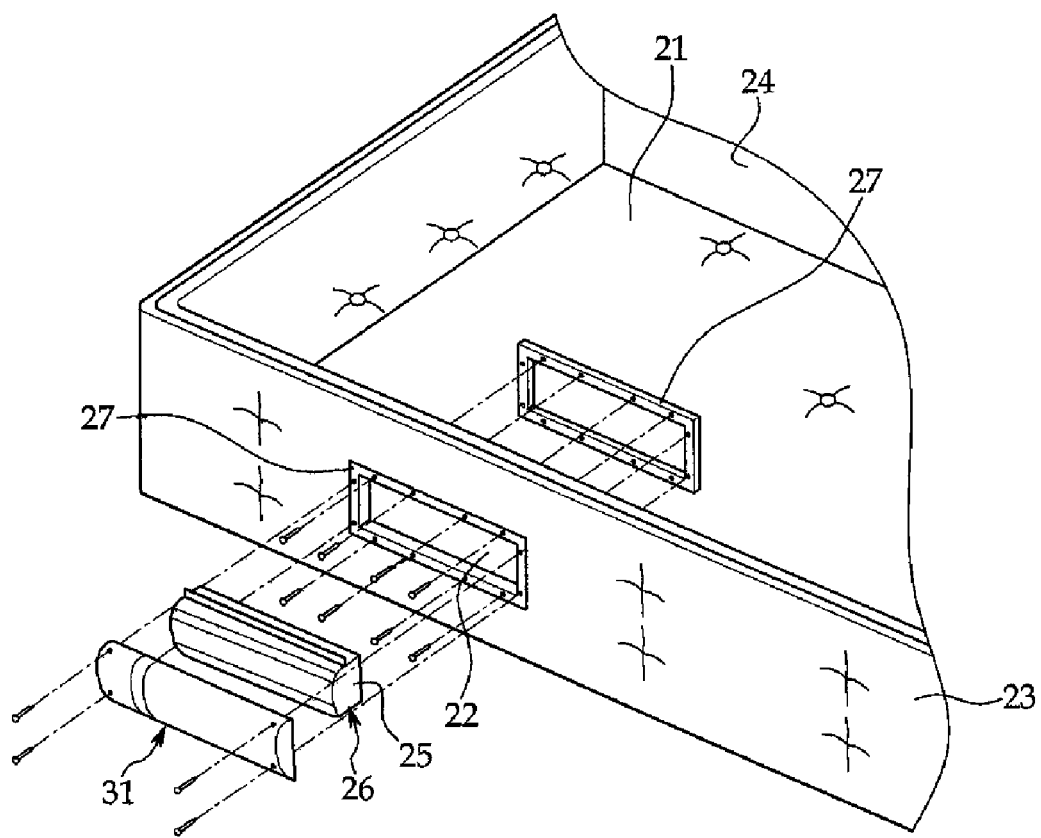
FIG. 2 is a view of a heating and sterilizing part according to an embodiment of the present invention.
Figure 3:
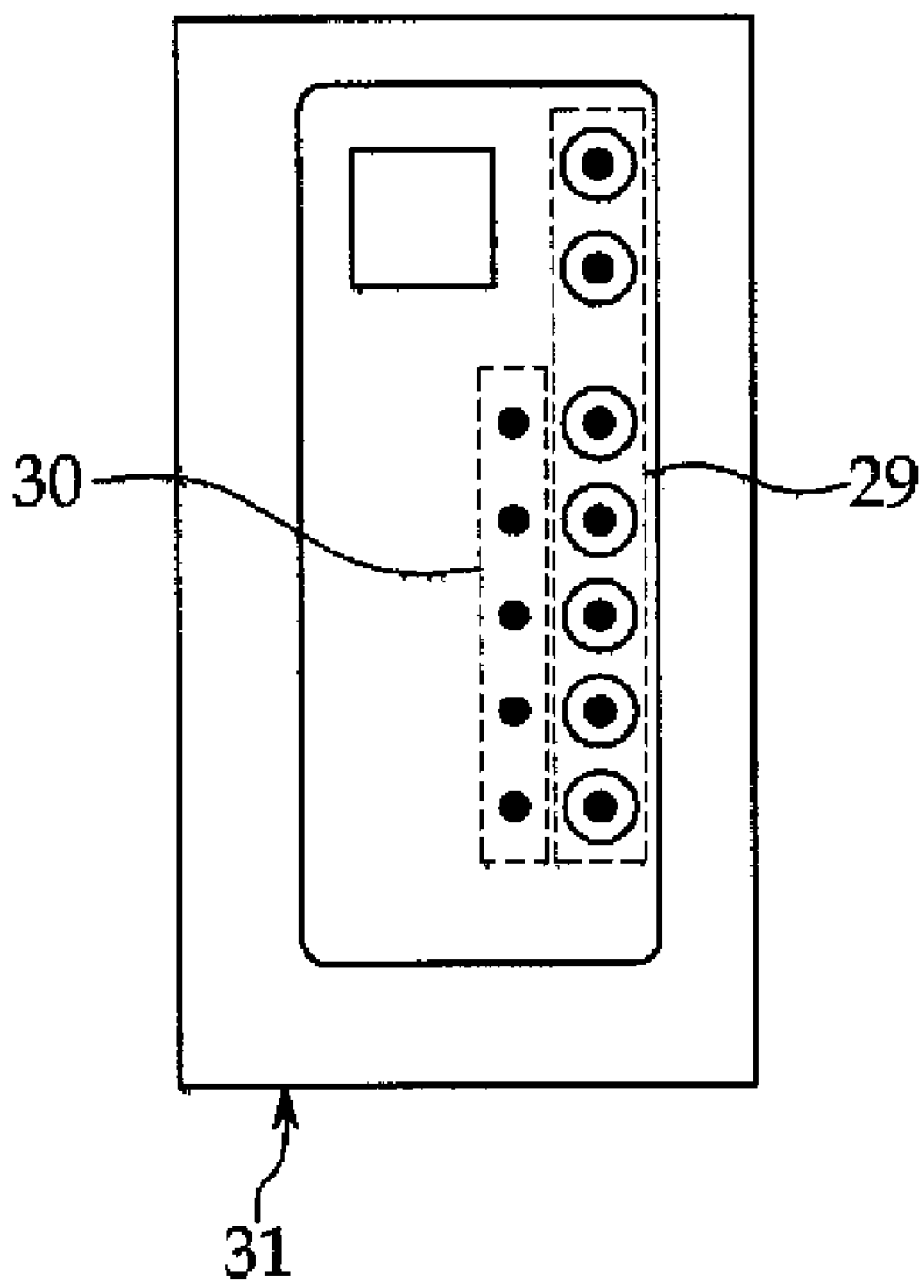
FIG. 3 is a view of an external operation controller according to an embodiment of the present invention.
Figure 4:
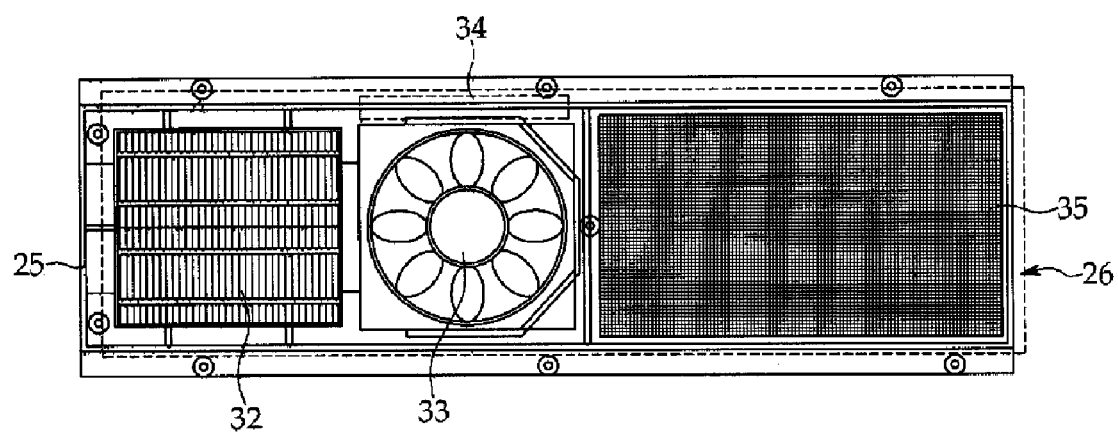
FIG. 4 is a bottom view of the heating and sterilizing part according to an embodiment of the present invention.
Figure 5:
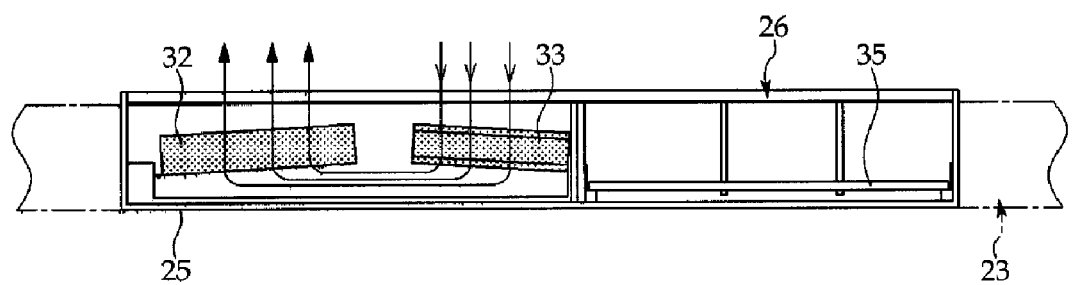
FIG. 5 is a plan view of the heating and sterilizing part according to an embodiment of the present invention, and illustrates an air flow within the heating and sterilizing part.
Figure 6:
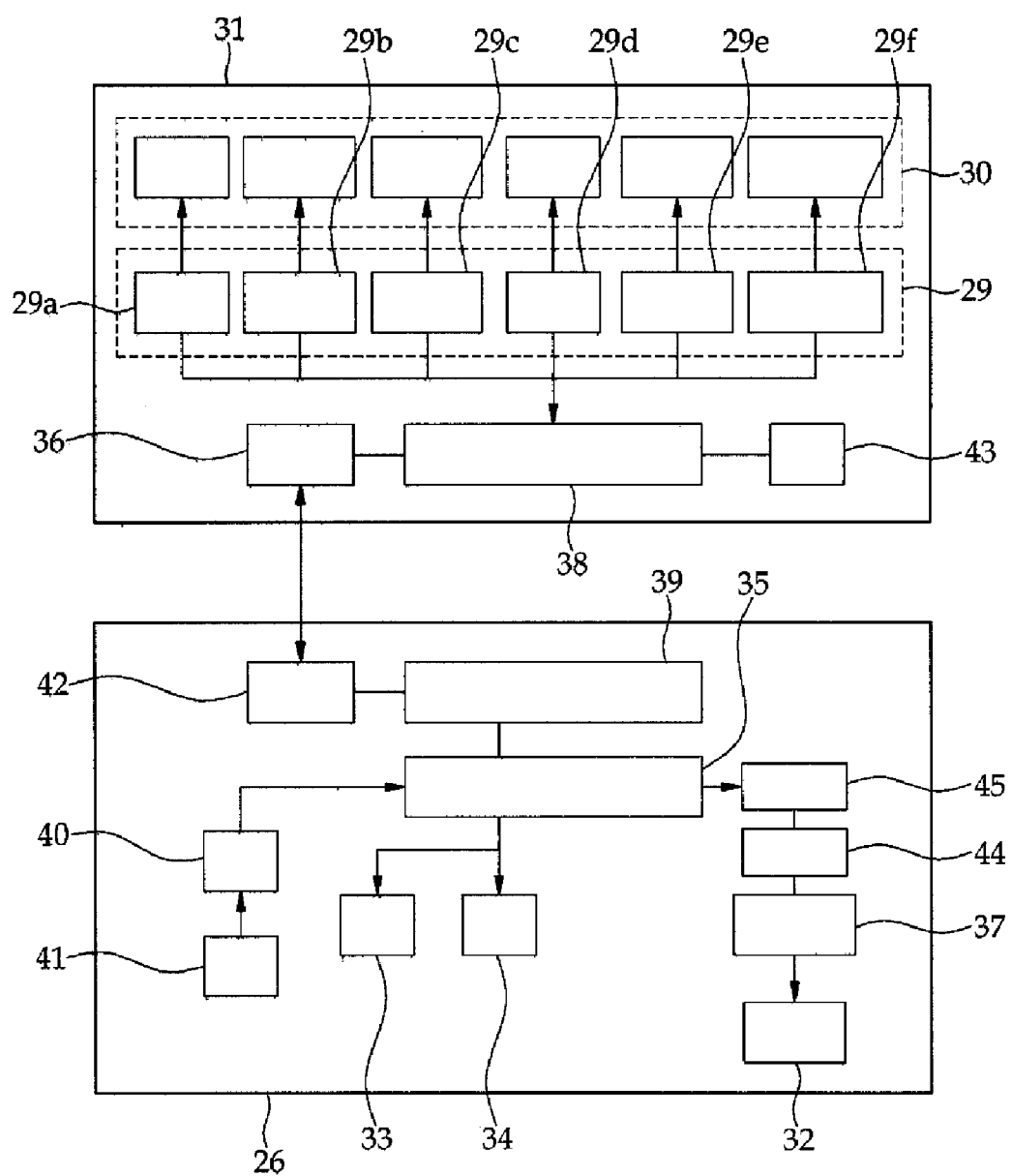
FIG. 6 is a block diagram of main parts according to an embodiment of the present invention.
Figure 7:
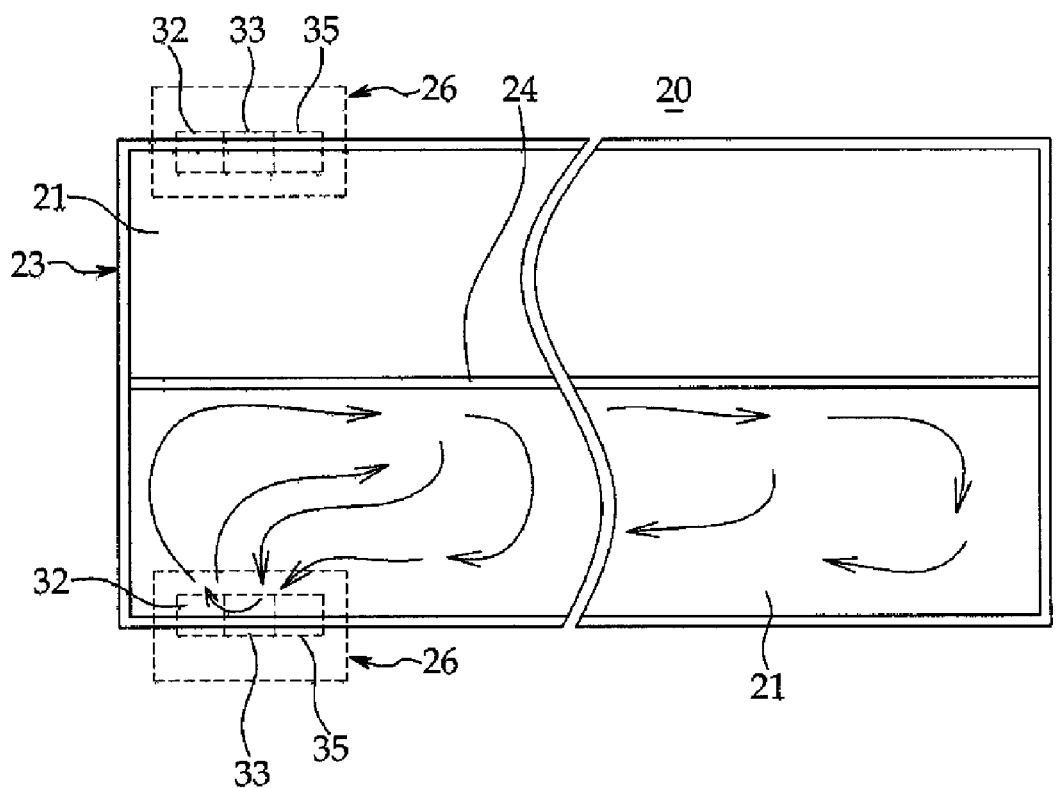
FIG. 7 is a view of an air flow within the bed mattress according to an embodiment of the present invention.

FIG. 1 is a perspective view of a bed mattress according to an embodiment of the present invention. FIG. 2 is a view of a heating and sterilizing part according to an embodiment of the present invention. FIG. 3 is a view of an external operation controller according to an embodiment of the present invention. FIG. 4 is a bottom view of the heating and sterilizing part according to an embodiment of the present invention. FIG. 5 is a plan view of the heating and sterilizing part according to an embodiment of the present invention, and illustrates an air flow within the heating and sterilizing part. FIG. 6 is a block diagram of main parts according to an embodiment of the present invention. FIG. 7 is a view of an air flow within the bed mattress according to an embodiment of the present invention.

A heating and sterilizing apparatus for a bed mattress includes a bed mattress 20. The bed mattress 20 includes a surface sheet 11 constituting a top surface 10 and a built-in elastic member 12 for elastically supporting the surface sheet 11. Also, the bed mattress 20 has walls forming a front surface 13, a rear surface 14, and both side surfaces 15.

Specifically, the heating and sterilizing apparatus includes a mattress body 23, a partition 24, a case 25, and a heating and sterilizing part 26. An inner space 21 is defined inside the mattress body 23, and a portion of either side surface 15 of the mattress body 23 is cut to define a hole 22 for installing the heating and sterilizing part 26. The partition 24 is disposed inside the mattress body 23 to partition the inner space 21 defined inside the mattress body 23. The case 25 is disposed on the hole 22 defined in the mattress body 23. The heating and sterilizing part 26 is disposed in the case 25 to heat and sterilize the inner space 21 of the mattress body 23 partitioned by the partition 24 and calculate air within the inner space 21 of the mattress body 23.

Installation brackets 27 for fixing and fitting the case 25 may be disposed on inner and outer surfaces of the mattress body 23 corresponding to the hole 22. The heating and sterilizing part 26 may be firmly assembled with the mattress body 23 by the installation brackets 27 disposed on the inner and outer surfaces of the mattress body 23 corresponding to the hole 22.

The partition 24 may be longitudinally disposed along a length direction to symmetrically divide the inner space 21 of the mattress body 23 into both sides. Although the partition 24 is horizontally disposed as illustrated in FIG. 1, the partition 24 may be vertically disposed. Also, although the partition 24 symmetrically divides the inner space 21 of the mattress body 23 into two equal portions as illustrated in FIG. 1, the inner space 21 of the mattress body 23 may be divided into a plurality of equal portions, e.g., three equal portions, according to the number and a position of the partition 24.

The partition 24 may be formed of one of flame resistant urethane foams, cloths, and synthetic resins. Specifically, the partition 24 may be formed of a material having low thermal deformation to prevent the partition 24 from being deformed and fired.

For example, two heating and sterilizing parts 26 may be disposed in two holes 22 defined in both side surfaces 15 of the mattress body 23, respectively. In drawings, a case in which the heating and sterilizing parts 26 are separately disposed in the inner spaces 21 of the mattress body 23 divided into two equal portions by the one partition 24, respectively, is described as an example.

As shown in FIGS. 2 and 3, an external operation controller 31 including an operation panel 29 and an operation condition display panel 30 may be disposed outside the case 25 disposed on the mattress body 23.

The external operation controller 31 may be wiredly or wirelessly connected to the heating and sterilizing part 26. Here, the external operation controller 31 may be directly disposed on a front surface of the case 25. Alternatively, the external operation controller 31 may be separated from the case 25 in a separate remote control type. That is, as described above, the external operation controller 31 is a kind of controller for controlling an operation of the heating and sterilizing part 26 or displaying an operation condition of the heating and sterilizing part 26. The external operation controller 31 may be integrally formed with the case 25 or separated from the case 25 in a remote control type. In case where the external operation controller 31 is integrally formed with the case 25, the external operation controller 31 may be connected to the heating and sterilizing part 26 through a direct connection terminal. In case where the external operation controller 31 is separated from the case 25, the operation of the heating and sterilizing part 26 may be confirmed and controlled using a wireless transmission method applicable for a general remote control operation method.

Referring to FIGS. 4 and 5, the heating and sterilizing part 26 may include a heater 32, an air-circulation fan 33, an ozone lamp 34, a temperature sensor 45, and an operation circuit part 35. The heater 32 is disposed inside the case 25 to adjust a temperature of the inner space 21 of the mattress body 23. The air-circulation fan 33 is disposed inside the case 25 to circulate air within the inner space 21 of the mattress body 23. The ozone lamp 34 is disposed at a central portion of the case 25 to generate ozone. The temperature sensor 45 detects a temperature of the inner space 21 of the mattress body 23. The operation circuit part 35 controls operations of the heater 32, the air-circulation fan 33, and the ozone lamp 34.

The heater 32 may heat and dehumidify the inner space 21 of the mattress body 23. In addition, a surface of the heater 32 may be coated with tourmaline to generate tourmaline anions when operated upon. The tourmaline is a material that radiates anions having a large amount of tourmaline components. Also, the tourmaline is known as a material that leads to human body cell's activation, metabolism stimulation, vitality boost, and fatigue recovery.

A positive temperature coefficient (P.T.C) aluminum wrinkle heater that is advantageous for overheat protection and heats air without preheating during an initial heating time may be used as the heater 32. The P.T.C heater has a higher heat dissipation rate, superior heat generation capacity, safety, and low power consumption when compared to line and coil-type heaters. In addition, when increased at a predetermined temperature, as a temperature increases by a phase transition, a resistance value may significantly increase to reduce a temperature of the P.T.C heater, thereby preventing the P.T.C heater from overheating. Also, the resistance value may significantly increase at a certain temperature (Curie temperature) to heat the air without preheating during the initial heating time.

The heating and sterilizing part 26 may include a temperature overheat sensor 37 in the inner space 21 of the mattress body 23. The temperature overheat sensor 37 may detect an overheat temperature of the inner space 21 of the mattress body 23 and checks the overheat temperature of the heater 32 to transmit a detection signal to the operation circuit part 35 and the external operation controller 31.

Also, the heating and sterilizing part 26 may include the operation circuit part 35, a power supply 40, a power input port 41, and a connection terminal block 42. The operation circuit part 35 operates a microprocessor 39, which shares data or a control signal with the external operation controller 31 and outputs resultant values to a microprocessor 38 of the external operation controller 31. The power supply 40 and the power input port 41 supply a power to the operation circuit part 35. The connection terminal block 42 is engagingly connected to a connection terminal block 36 of the external operation controller 31.

A power supply 43 is selectively provided in the external operation controller 31. The power supply 43 supplies a power to the microprocessor 39, which shares an input/output data signal with the microprocessor 38 of the heating and sterilizing part 26. When the external operation controller 31 is integrally formed with the case 25, a separate power supply is not required.

The operation panel 29 may include a power on/off key 29a, a heating on/off key 29b, a sterilizing on/off key 29c, a tourmaline on/off key 29d, a heating reservation set key 29e, and a heating temperature set key 29f. The operation condition display panel 30 may be disposed corresponding to the keys 29a, 29b, 29c, 29d, 29e, and 29f to display an operation condition of the heating and sterilizing part 26. Undescribed reference numeral '44' designates a temperature fuse.

An operation and effect of the heating and sterilizing apparatus for the bed mattress according to the present invention will be described below.

When a power is supplied through the power supply 40 of the heating and sterilizing part 26, the power is supplied to the operation circuit part 35 and the microprocessor 39. The microprocessor 39 operates the air-circulation fan 33, the heater 32, and the ozone lamp 34, which are functional parts, according to a preset program. Here, an operation period and time of the air-circulation fan 33, the heater 32, and the ozone lamp 34 may be previously set, and a heating temperature and a reservation temperature may previously set also.

The heater 32 is disposed on the case 25 to generate heat when the power is applied. When the air-circulation fan 33 is operated, air within the inner space 21 of the mattress body 23 is introduced into the air-circulation fan 33. The air introduced into the air-circulation fan 33 is discharged from the inside of the case via the heater 32. In this process, a temperature of the air increases by the heater 32, and the heated air flows into the inner space 21 of the mattress body 23. Thus, the inner space 21 of the mattress body 23 is heated by the increased air temperature.

When a temperature of the heater 32 increases, the heater 32 coated with tourmaline radiates the tourmaline anions while heating. A radiation amount of the tourmaline anions is varied according to a heating temperature of the heater 32.

A flow range of the air introduced into the inner space 21 of the mattress body 23 by the air-circulation fan 33 is limited to a portion, at which the heating and sterilizing part 26 is disposed, due to the partition 24 partitioning the inner space 21 of the mattress body 23.

As shown in FIG. 1, when the partition 24 is disposed inside the mattress body 23, the heating and sterilizing parts 26 should be disposed in both sides with respect to the partition 24, respectively, so as to separately heat and sterilize the both sides. Thus, only one side with respect to the partition 24 may be heated and sterilized, and the both sides may be heated and sterilized. Also, the one side and the both sides may be alternately heated and sterilized according to an operation mode. As described above, since the partition 24 may be disposed inside the mattress body 23, and only a portion of the entire surface of the mattress body 23 may be selectively heated and sterilized, a heating area may be reduced according to a user's selection to reduce the power consumption.

Also, the heater 32 may be coated with tourmaline powder when the heater 32 is manufactured. Thus, when the heater 32 is operated, the heater 32 generates the tourmaline anions to stimulate metabolism of human body cells, boost vitality, and recover fatigue due to tourmaline anion effects during the bed mattress life. Thus, the user keeps a healthy bed life. In addition, since the ozone may be generated through the ozone lamp 34 to prevent bacteria and molds within the inner space 21 of the mattress body 23 from being propagated, and simultaneously, to remove stench, the bed mattress may be maintained in the clean state for a long time.

According to the present invention, when the bed mattress is heated, the temperature of the mattress can be separately adjusted according to the user's setting to cooperate with the heating or independently control the double bed mattress. In addition, the anions are ozone can be generated to prevent the bacteria and molds from being propagated. Also, the split heating mode or simultaneous heating mode can be selected to always maintain the bed mattress in the warm and clean state. Therefore, the bed mattress can be comfortably and cleanly used at all times. Also, a bed mattress that can be heated during the winter without causing harmful effects to the human body can be manufactured.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalents of such metes and bounds are therefore intended to be embraced by the appended claims.

What is claimed is:

1. A fixed bed mattress having a heating and sterilizing apparatus configured to form a closed system with air inside the fixed bed mattress, comprising:
   a fixed bed mattress of generally constant size that cannot collapse or deflate to a compacted size for storage or transportation between use, the fixed bed mattress having a body defining an inner space, the body defining an installation hole in a side surface thereof;
   a surface sheet forms a top surface of the fixed bed mattress;
   a built-in elastic member for elastically supporting the surface sheet of the fixed bed mattress such that the surface sheet is configured to support a person thereon without requiring additional force directed generally outwardly on an inner surface of the surface sheet;
   the heating and sterilizing apparatus is disposed on the fixed bed mattress and comprises:
   a case disposed on the installation hole defined in the body; and
   a heating and sterilizing part disposed in the case to heat and sterilize the inner space of the mattress body that is in fluid communication with the heating and sterilizing part by circulating air within the body, wherein the air that is circulated by the heating and sterilizing apparatus is drawn from and driven into the fixed bed mattress so as to generally form a closed air circulation system inside the fixed bed mattress, the operation of the heating and sterilizing part and the associated driving of circulated air not being necessary for the fixed bed mattress to normally support a person thereon.

2. The fixed bed mattress of claim 1, wherein a partition is disposed within the body and along a longitudinal direction of the fixed bed mattress to symmetrically divide the inner space of the mattress body into two sides.

3. The fixed bed mattress of claim 1, wherein the heating and sterilizing part comprises:
   a heater disposed inside the case to adjust a temperature of the inner space of the mattress body;
   an air-circulation fan disposed inside the case to circulate air within the inner space of the mattress body;
   an ozone lamp disposed at a central portion of the case to generate ozone;
   a temperature sensor detecting a temperature of the inner space of the mattress body; and
   an operation circuit part controlling operations of the heater, the air-circulation fan, and the ozone lamp.

4. The fixed bed mattress of claim 3, wherein the heater comprises a positive temperature coefficient (P.T.C) heater, which is advantageous for overheat protection and heats the air without preheating during an initial heating time.

5. The fixed bed mattress of claim 3, wherein the heating and sterilizing part comprises a temperature overheat sensor in the inner space of the mattress body to detect an overheat temperature of the inner space of the mattress body and check the overheat temperature of the heater, thereby to transmit a detection signal to the operation circuit part and the external operation controller.

6. The fixed bed mattress of claim 3, wherein there are two of the heating and sterilizing part disposed on the body.

7. The fixed bed mattress of claim 1, wherein an external operation controller including an operation panel and an operation condition display panel is disposed outside the case disposed on the mattress body.

8. The fixed bed mattress of claim 7, wherein the external operation controller is connected to the heating and sterilizing part through one of a wire connection and a wireless connection.

9. The fixed bed mattress of claim 3, wherein the heater is coated with tourmaline to generate anions when the heater is operated.

10. The fixed bed mattress of claim 2, wherein the partition is formed of at least one of flame resistant urethane foams, cloths, and synthetic resins.

11. The fixed bed mattress of claim 1, wherein a plurality of installation brackets for fixing and fitting the case are disposed on the body proximate to the installation hole.

12. A fixed bed mattress having a heating and sterilizing apparatus, comprising:
   a fixed bed mattress of generally constant size that cannot collapse or deflate to a compacted size for storage or transportation between use; the fixed bed mattress having a body defining an inner space, the mattress body having an installation hole, in which a portion of either side surface thereof is cut;
   a surface sheet constituting a top surface of the fixed bed mattress;
   a built-in elastic member for elastically supporting the surface sheet of the fixed mattress such that the surface sheet is configured to support a person thereon without requiring additional force directed generally outwardly on an inner surface of the surface sheet;
   a the heating and sterilizing apparatus comprising:
   a case disposed on the installation hole defined in the body; and
   the heating and sterilizing part disposed in the case to heat and sterilize the inner space of the mattress body in fluid communication with the installation hole by circulating air within the rigid mattress body, the operation of the heating and sterilizing part and the associated driving of circulated air not being necessary for the fixed bed mattress to normally support a person thereon, the heating and sterilizing part comprising:
   a heater disposed inside the case to adjust a temperature of the inner space of the mattress body;
   an air-circulation fan disposed inside the case to circulate air within the inner space of the mattress body;
   an ozone lamp disposed at a central portion of the case to generate ozone;
   a temperature sensor detecting a temperature of the inner space of the mattress body; and
   an operation circuit part controlling operations of the heater, the air-circulation fan, and the ozone lamp.

* * * * *